(12) United States Patent
Kanazawa et al.

(10) Patent No.: US 8,087,781 B2
(45) Date of Patent: Jan. 3, 2012

(54) OPTOTYPE PRESENTING APPARATUS

(75) Inventors: Yuichiro Kanazawa, Okazaki (JP); Tatefumi Oda, Nukata-gun (JP)

(73) Assignee: Nidek Co., Ltd., Gamagori-shi (JP)

( * ) Notice: Subject to any disclaimer, the term of this patent is extended or adjusted under 35 U.S.C. 154(b) by 320 days.

(21) Appl. No.: 12/232,797

(22) Filed: Sep. 24, 2008

(65) Prior Publication Data

US 2009/0086166 A1   Apr. 2, 2009

(30) Foreign Application Priority Data

Oct. 1, 2007  (JP) ................................ 2007-258167

(51) Int. Cl.
*A61B 3/02* (2006.01)

(52) U.S. Cl. ......... 351/240; 351/222; 351/237; 351/239

(58) Field of Classification Search ................ 351/200, 351/211, 237, 239, 222, 232, 240, 243, 201; 348/263, E13.038; 382/167
See application file for complete search history.

(56) References Cited

U.S. PATENT DOCUMENTS

| | | | |
|---|---|---|---|
| 5,638,082 A | | 6/1997 | Grimm |
| 2004/0036840 A1 * | | 2/2004 | Marino et al. ............... 351/239 |
| 2004/0076942 A1 | | 4/2004 | O'Neil et al. |
| 2005/0105050 A1 * | | 5/2005 | Hosoi ......................... 351/235 |
| 2008/0002153 A1 | | 1/2008 | Kanazawa et al. |
| 2008/0018858 A1 | | 1/2008 | Kanazawa et al. |

FOREIGN PATENT DOCUMENTS

| | | |
|---|---|---|
| JP | A-5-130975 | 5/1993 |
| JP | A-2006-42978 | 2/2006 |
| JP | A-2007-296100 | 11/2007 |
| JP | A-2008-6115 | 1/2008 |
| JP | A-2008-23129 | 2/2008 |
| WO | WO 95/10219 | 4/1995 |
| WO | WO 2007/109760 A2 | 9/2007 |

OTHER PUBLICATIONS

European Search Report dated Jun. 22, 2010 from European Application No. EP 08165166.3.

* cited by examiner

*Primary Examiner* — Ricky Mack
*Assistant Examiner* — Mahidere S Sahle
(74) *Attorney, Agent, or Firm* — Oliff & Berridge, PLC

(57) ABSTRACT

An optotype presenting apparatus, by which red and green optotypes can be visually perceived independently by right and left eyes even if red filters and/or green filters have different wavelength transmission characteristics, comprises a color display, a unit having a switch for selecting a test chart including visual acuity and red-green binocular visual performance test charts, wherein the binocular test chart includes the optotypes and is used in the test performed with the filters in front of the eyes, a memory storing color adjustment data in which at least one of color tones of the optotypes is varied with the characteristic of one of the filters, a unit for inputting a signal for selecting one of the data, and a unit controlling the display to display the selected chart and adjusting the tones by reading the selected data from the memory when the binocular test chart is selected.

11 Claims, 7 Drawing Sheets

| chart | High/Low |
|---|---|
| VA charts | 0 |
| Worth | 1 |
| Phoria | 1 |
| Red-Green | 0 |
| Polarized Red-Green | 0 |
| Vertical coincidence | 1 |
| Schober | 1 |
| Dots | 0 |
| Cyclophoria | 1 |
| Phoria with fixation | 1 |
| Stereo | 1 |
| Exact Stereo | 1 |
FIG. 7
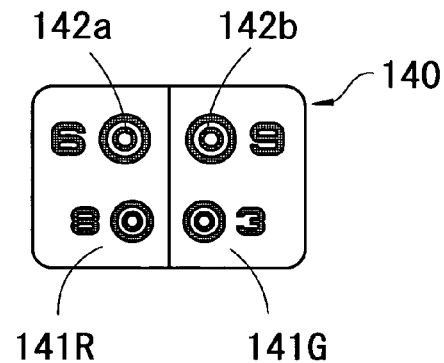
FIG. 8
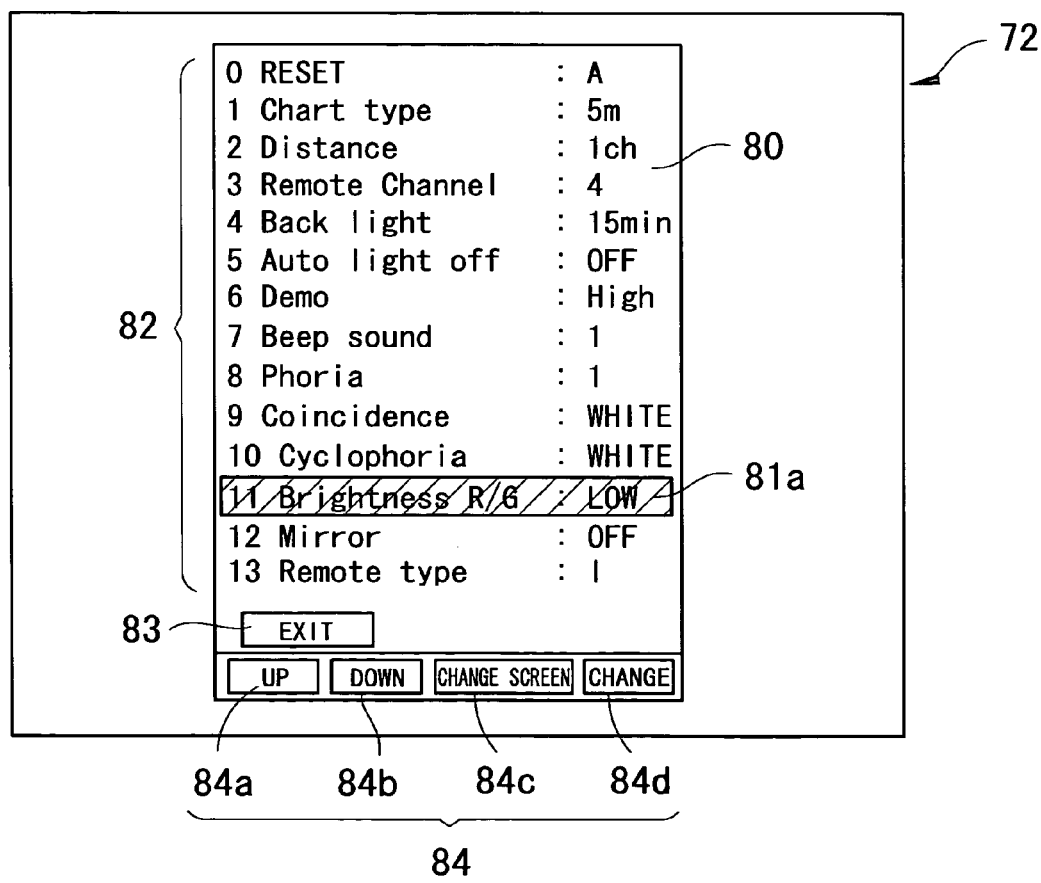
FIG. 9

OPTOTYPE PRESENTING APPARATUS

BACKGROUND OF THE INVENTION

1. Field of the Invention

The present invention relates to an optotype presenting apparatus which presents an optotype and/or a test chart for testing visual acuity and binocular visual performance of eyes of an examinee.

2. Description of Related Art

Conventionally, there are known an optotype presenting apparatus such that an optotype and/or a test chart drawn on a disk is illuminated from behind with a light source such as a halogen lamp and the optotype and/or the test chart is projected onto a screen at a far distance for a test of such as 5 meters, and an optotype presenting apparatus having a display such as a color liquid crystal display (see Japanese Patent Application Unexamined Publication No. Hei 05-130975 corresponding to U.S. Pat. No. 5,638,082, and Japanese Patent Application Unexamined Publication No. 2006-42978).

Examples of the test chart presented by the optotype presenting apparatus include a visual acuity test chart used in a refractive power test (see FIG. 1), a red-green test chart for testing overcorrection, a phoria test chart, a fusion test chart, and a stereoscopic vision test chart, which are test charts for testing binocular visual performance by making right and left eyes respectively observe different optotypes. The binocular visual performance test chart includes a red-green binocular visual performance test chart such that different optotypes are presented to right and left eyes of an examinee with a red filter placed in front of one of the eyes and a green filter placed in front of the other eye.

FIGS. 3A to 3D show an example of a Worth four-point chart used for testing fusion and suppression of eyes. In FIG. 3A, a Worth four-point chart (test chart) 100 includes, on a black background 101, a circular red optotype 102 on the upper side, circular green optotypes 104 and 105 respectively on the left side and the right side, and a circular white optotype 103 on the lower side. When the test chart 100 is observed through a red filter placed in front of a right eye, the red optotype 102 and the white optotype 103 are visually perceived in red as shown in FIG. 3B. Meanwhile, the green optotypes 104 and 105 are visually perceived in black and appear merged with the black background 101 because green light therefrom is cut off by the red filter. In addition, when the test chart 100 is observed through a green filter in front of a left eye, the red optotype 102 is visually perceived in black and appears merged with the black background 101 as shown in FIG. 3C because red light therefrom is cut off by the green filter. Meanwhile, the green optotypes 104 and 105 and the white optotype 103 are visually perceived in green. When the test chart 100 is observed by both of the eyes, it is judged that the left eye is suppressed if the optotypes are visually perceived in the state shown in FIG. 3B, and it is judged that the right eye is suppressed if the optotypes are visually perceived in the state shown in FIG. 3C. In addition, if fusion is proper, the red optotype 102 and the green optotypes 104 and 105 are simultaneously visually perceived, and the white optotype 103 is visually perceived alternately in red and green.

For respectively placing the red filter and the green filter in front of the eyes, a subjective refractive power measurement apparatus capable of switching between a red filter and a green filter to be respectively placed in right and left test windows, or red and green spectacles with a red filter and a green filter are used.

However, red filters to be used in the subjective refractive power measurement apparatus and the red and green spectacles have different wavelength transmission characteristics even if they are similarly red. Green filters also have different wavelength transmission characteristics in some cases. These differences result from different apparatus manufacturers, or even when the red filters and/or the green filters are produced by one apparatus manufacturer, there are variations between the red filters and/or between the green filters. Therefore, there is a problem that when a subjective refractive power measurement apparatus or red and green spectacles are used, a green optotype and a red optotype are not visually perceived independently by right and left eyes, and the optotypes do not partly merge with the background and are unintentionally visually perceived by unintended eyes. For example, in the test chart 100 shown in FIG. 3A, when the test chart 100 is observed through the red filter, the green optotypes 104 and 105 do not merge with the background 101 and are unintentionally visually perceived in light green as shown in FIG. 3D. In such a case, the binocular visual performance test cannot be accurately performed.

SUMMARY OF THE INVENTION

An object of the invention is to overcome the problems described above and to provide an optotype presenting apparatus by which a red optotype and a green optotype of a red-green binocular visual performance test chart can be visually perceived independently by right and left eyes even if a red filter and/or a green filter used in a binocular visual performance test have different wavelength transmission characteristics, so that the binocular visual performance test can be more accurately performed.

To achieve the objects and in accordance with the purpose of the present invention, an optotype presenting apparatus has a color display which displays a test chart, a test chart selecting unit which has a switch for selecting the test chart including a visual acuity test chart and a red-green binocular visual performance test chart, wherein the binocular visual performance test chart includes a red optotype and a green optotype and is used in a binocular visual performance test performed with a red filter placed in front of one of eyes of an examinee and a green filter placed in front of the other eye, a memory which stores a plurality of color adjustment data in which at least one of a color tone of the red optotype and a color tone of the green optotype is varied in accordance with a wavelength transmission characteristic of one of the red filter and the green filter, a color adjustment data selecting unit with which a selection signal for selecting one of the plurality of color adjustment data stored in the memory is inputted, and a display control unit which controls the display to display the selected test chart and adjusts at least one of the color tone of the red optotype and the color tone of the green optotype to be displayed on the display by reading the selected color adjustment data from the memory when the binocular visual performance test chart is selected.

Additional objects and advantages of the invention are set forth in the description which follows, are obvious from the description, or may be learned by practicing the invention. The objects and advantages of the invention may be realized and attained by the optotype presenting apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 7 is a table showing test charts subjected to switching between a High mode and a Low mode;

FIG. 8 is a view showing an example of a red-green test chart for testing overcorrection at the time of a refractive power test;

FIG. 9 is a view showing a parameter setting screen to be displayed on the LCD.

DETAILED DESCRIPTION OF THE PREFERRED EMBODIMENTS

Figure 1:
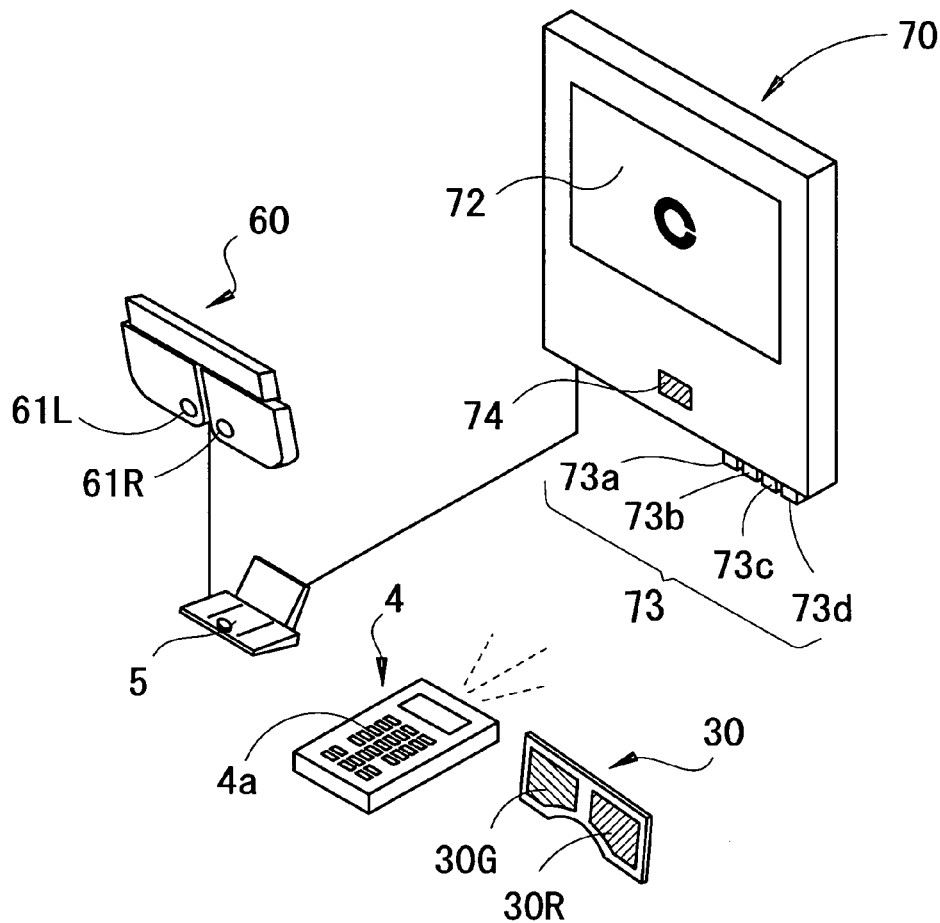
FIG. 1 is a schematic view showing an optotype presenting apparatus according to preferred embodiment of the present invention.
Figure 2:
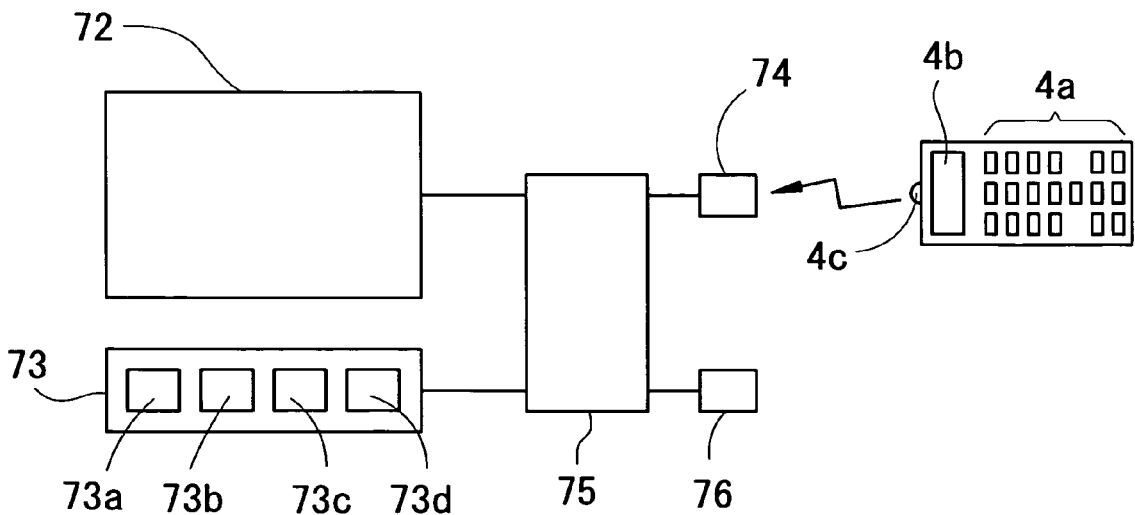
FIG. 2 is a control block diagram of the optotype presenting apparatus.

A detailed description of one preferred embodiment of an optotype presenting apparatus embodied by the present invention is provided below with reference to the accompanying drawings. FIG. 1 is a schematic view showing the optotype presenting apparatus, and FIG. 2 is a control block diagram of the optotype presenting apparatus. As shown in FIG. 1, an optotype presenting apparatus 70 comprises a color liquid crystal display (LCD) 72 on a front surface of its cabinet, and a receiving unit 74 which receives a light signal from a remote controller 4. In addition, the optotype presenting apparatus 70 comprises a function switch 73 consisting of four switches 73a to 73d on an under surface of its cabinet. The function switch 73 is used as an operating unit for displaying a parameter setting screen on the LCD 72 and setting parameters.

Display on the LCD 72 is controlled by a control unit 75. In the LCD 72, a number of pixels are geometrically arranged, and each of the pixels comprises a filter which transmits any one of specific wavelengths of red, green and blue (hereinafter, referred to as an RGB filter). Color tones of a test chart to be displayed on the LCD 72 are varied by controlling intensity of light transmitted through the RGB filters of the respective pixels by the control unit 75. The control unit 75 is connected with the function switch 73 and a memory 76. The memory 76 stores configuration data of the test chart and setting data on color adjustment (luminance and hue) of the test chart.

The remote controller 4 comprises a number of test chart selecting switches 4a for selecting a test chart, a display 4b which displays information on the selected test chart, and a transmitting portion 4c which transmits a selection signal of the test chart in the form of a light signal. In addition, in the case of using a subjective refractive power measurement apparatus 60 in the test, an operating unit 5 for the subjective refractive power measurement apparatus 60 is connected to the control unit 75. In the subjective refractive power measurement apparatus 60, correction lenses and various optical elements are selectively placed in right and left test windows 61R and 61L.

Figure 3A:
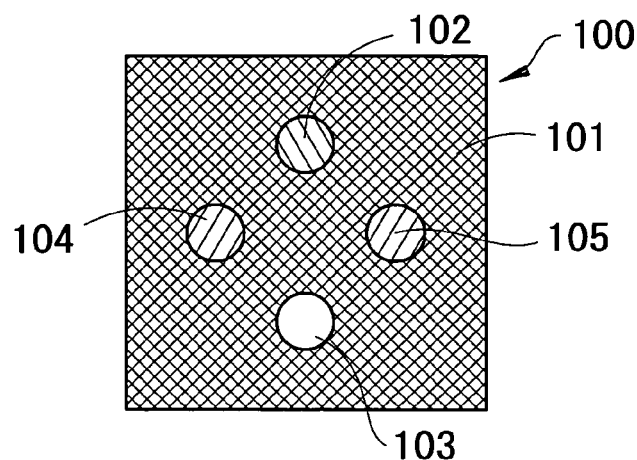
FIGS. 3A to 3D are views showing an example of a red-green binocular visual performance test chart with a black background.
Figure 3B:
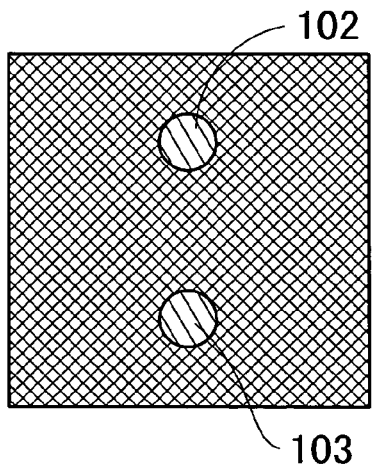
Figure 3C:
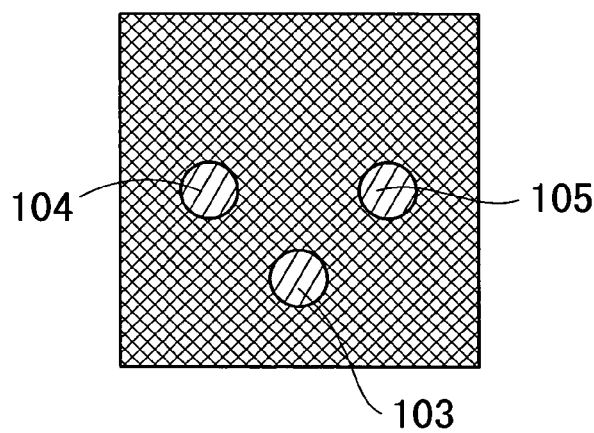
Figure 3D:
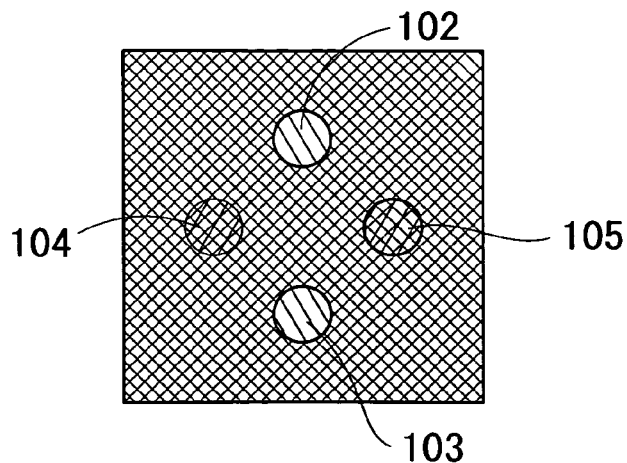

Examples of the test chart to be displayed on the LCD 72 of the optotype presenting apparatus 70 include a visual acuity test chart for a refractive power test, a red-green test chart for testing overcorrection, and a red-green binocular visual performance test chart including red and green optotypes for a binocular visual performance test (see FIG. 3A for example). When the red-green binocular visual performance test chart is displayed on the LCD 72, red and green spectacles 30 in which a red filter 30R is placed on the right eye side and a green filter 30G is placed on the left eye side are used. When the subjective refractive power measurement apparatus 60 is used, the red filter 30R is placed in the test window 61R for the right eye, and the green filter 30G is placed in the test window 61L for the left eye. Switching of the red filter 30R and the green filter 30G to be respectively placed in the test windows is executed by a given control signal from the operating unit 5.

FIGS. 3A to 4D show examples of the binocular visual performance test chart. FIGS. 3A to 3D shows a Worth four-point chart for testing fusion and suppression of eyes. To be specific, FIG. 3A shows a display state of the LCD 72 in which a Worth four-point chart (test chart) 100 comprises a black background 101, a circular red optotype 102 on the upper side, circular green optotypes 104 and 105 respectively on the left side and the right side, and a circular white optotype 103 on the lower side. When the test chart 100 is observed through the red filter 30R placed in front of the right eye, the red optotype 102 and the white optotype 103 are visually perceived in red as shown in FIG. 3B. Meanwhile, the green optotypes 104 and 105 are visually perceived in black and appear merged with the background 101 because green light therefrom is cut off by the red filter 30R. In addition, when the test chart 100 is observed through the green filter 30G placed in front of the left eye, the red optotype 102 is visually perceived in black and appears merged with the background 101 as shown in FIG. 3C because red light therefrom is cut off by the green filter 30G. Meanwhile, the green optotypes 104 and 105 and the white optotype 103 are visually perceived in green. When the test chart 100 is observed by both of the eyes, it is judged that the left eye is suppressed if the optotypes are visually perceived in the state shown in FIG. 3B, and it is judged that the right eye is suppressed if the optotypes are visually perceived in the state shown in FIG. 3C. In addition, if fusion is proper, the red optotype 102 and the green optotypes 104 and 105 are simultaneously visually perceived, and the white optotype 103 is visually perceived alternately in red and green. In addition, it is judged that diplopia occurs in the eyes if three bright spots by the optotypes are visually perceived (not shown).

Figure 4A:
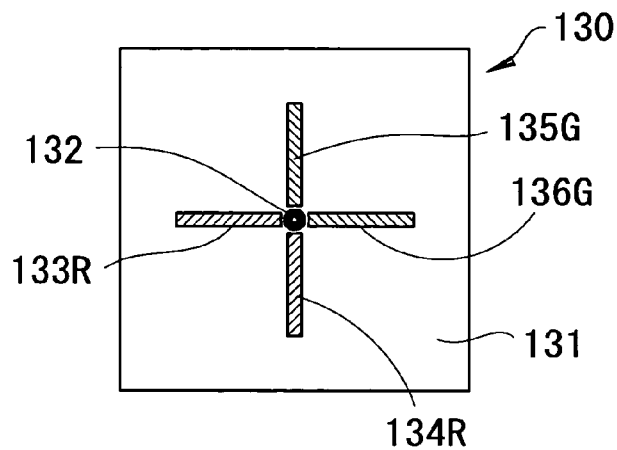
FIGS. 4A to 4D are views showing an example of a red-green binocular visual performance test chart with a white background.
Figure 4B:
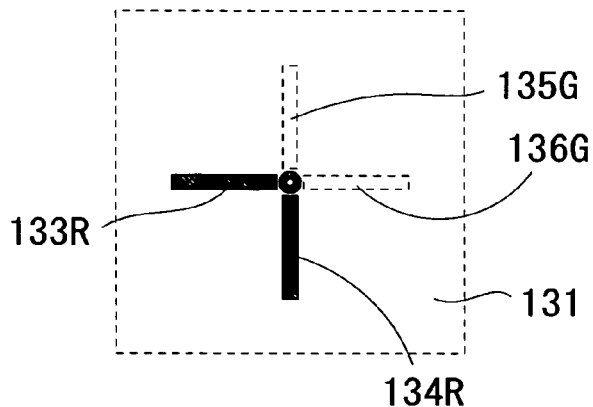

FIGS. 4A to 4D show a cross phoria test chart with a fixation target for a phoria test. A cross phoria test chart 130 with a fixation target shown in FIG. 4A comprises a white background 131, a fixation target 132 defining a black optotype located in the center of the background 131, a left-side horizontal line 133R defining a red optotype, a lower-side vertical line 134R defining a red optotype, an upper-side vertical line 135G defining a green optotype, and a right-side horizontal line 136G defining a green optotype. FIG. 4B shows a state when the phoria test chart 130 is observed through the green filter 30G. In this case, the background 131 is visually perceived in green because green light therefrom is transmitted through the green filter 30G. In addition, the upper-side vertical line 135G and the right-side horizontal line 136G are visually perceived in green because green light therefrom is transmitted through the green filter 30G. Thus, the upper-side vertical line 135G and the right-side horizontal line 136G merge with the background 131, so that their shapes cannot be recognized. Meanwhile, the left-side horizontal line 133R and the lower-side vertical line 134R are visually perceived in black because red light therefrom cannot be transmitted through the green filter 30G.

Figure 4C:
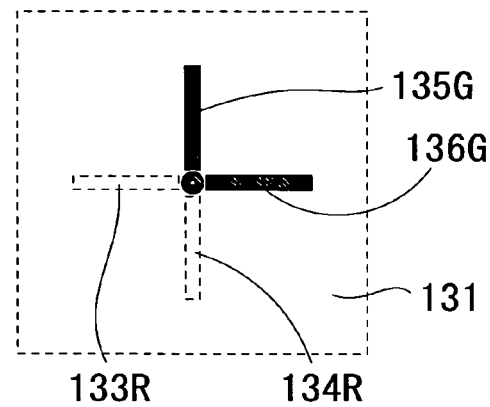
Figure 4D:
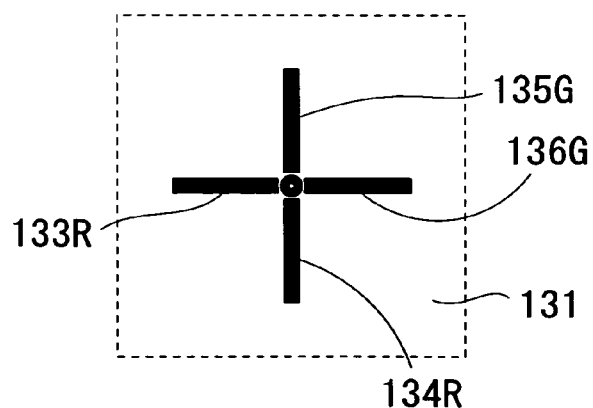

FIG. 4C shows a state when the test chart 130 is observed through the red filter 30R. In this case, the background 131 is visually perceived in red, and the left-side horizontal line 133R and the lower-side vertical line 134R merge with the background 131, so that their shapes cannot be recognized. Meanwhile, the upper-side vertical line 135G and the right-side horizontal line 136G are visually perceived in black because green light therefrom cannot be transmitted through the red filter 30R. The black fixation target 132, which does not have either of a red component and a green component, is visually perceived in black in each of the states shown in FIGS. 4B and 4C.

As described above, the optotypes are visually perceived differently through the red filter 30R and the green filter 30G. Therefore, the phoria test can be performed on the eyes of an examinee by using the fixation target 132 as a fusion optotype. In the case of emmetropia, the optotypes are visually perceived in a state shown in FIG. 4D which is a superposition of the states shown in FIGS. 4B and 4C. However, in the case of horizontal phoria, there is visually perceived a horizontal deviation between the upper-side vertical line 135G and the right-side horizontal line 136G, and the left-side horizontal line 133R and the lower-side vertical line 134R.

The red-green binocular visual performance test chart as described above was observed through a red filter 30R and a green filter 30G used in a subjective refractive power measurement apparatus 60. In the case of the test chart 100 shown in FIG. 3A, the green optotypes 104 and 105 did not merge with the background 101 and were inadvertently visually perceived in light green. In addition, in the case of the test chart 130 shown in FIG. 4A, when observed through the red filter 30R, the left-side horizontal line 133R and lower-side vertical line 134R were visually perceived in brighter red than the background 131, and there was visually perceived a difference against the background 131. Meanwhile, the upper-side vertical line 135G and the right-side horizontal line 136G were visually perceived not in black similar to the fixation target 132 but in black slightly including a green component. If the optotypes do not merge with the background (i.e., if the optotypes do not disappear) as described above, accuracy in the binocular visual performance test is impaired.

Figure 5A:
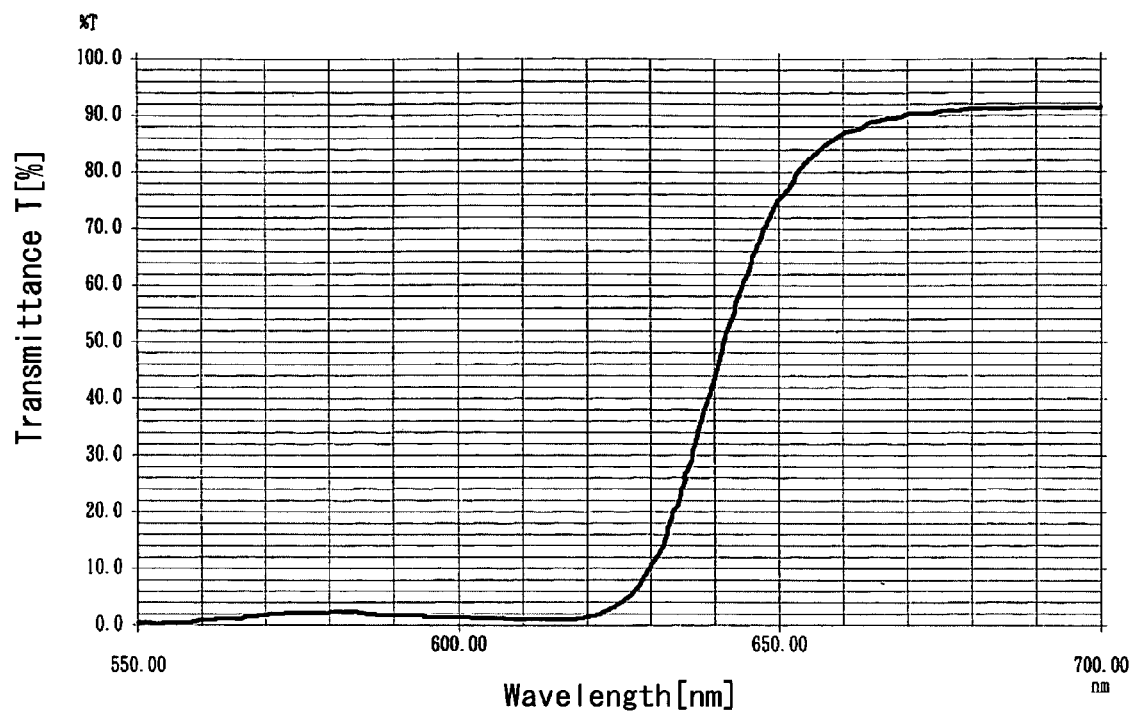
FIG. 5A is a graph showing a wavelength transmission characteristic of a red filter with problems.
Figure 5B:
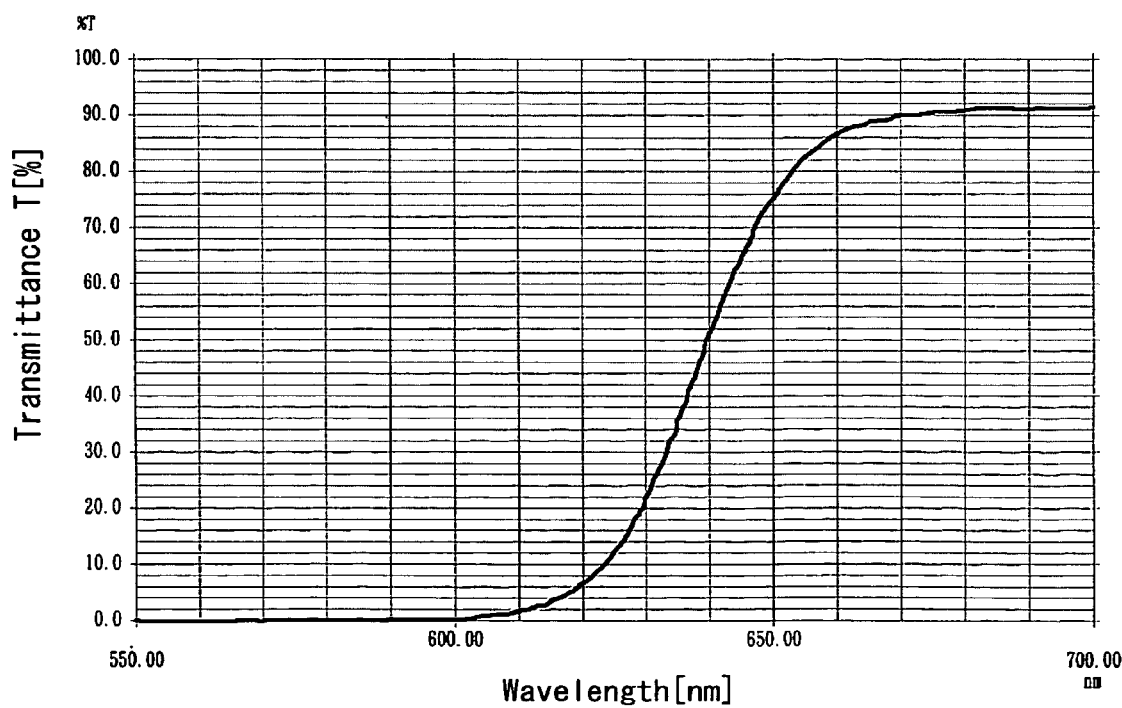
FIG. 5B is a graph showing a wavelength transmission characteristic of a red filter with no problems.
Figure 6:
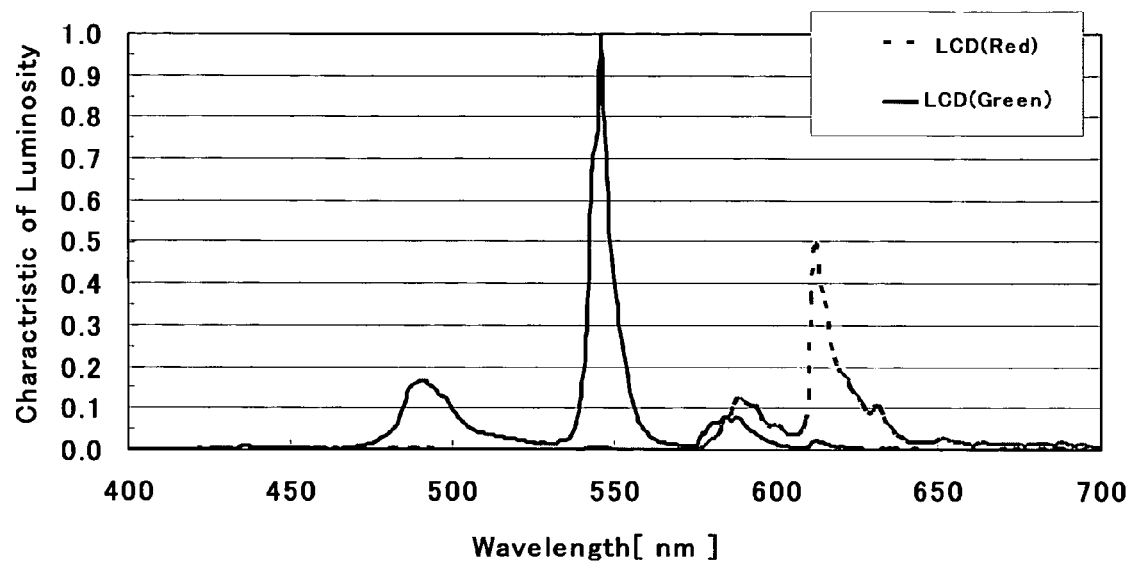
FIG. 6 is a graph showing a characteristic of luminosity when an LCD is controlled to emit only green light and a characteristic of luminosity when the LCD is controlled to emit only red light.

FIG. 5A is a graph showing a result of checking a wavelength transmission characteristic of the red filter 30R used in the apparatus 60 with problems as described above. FIG. 5B is a graph showing a result of checking a wavelength transmission characteristic of the red filter 30R used in the apparatus 60 with no problems. FIG. 6 is a graph showing a result of checking a characteristic of luminosity when the LCD 72 is controlled to emit only green light, and a characteristic of luminosity when the LCD 72 is controlled to emit only red light. RGB components of the optotypes to be displayed on the LCD 72 can be varied in their luminance levels from a level 0 to a level 31. The luminance levels of the green display were set so that (R,G,B)=(0,31,0), and those of the red display were set so that (R,G,B)=(31,0,0).

Referring to FIG. 5B showing the wavelength transmission characteristic of the red filter 30R with no problems, transmittance was constantly 0% in a wavelength range of 600 nm or less. In contrast, referring to FIG. 5A showing the wavelength transmission characteristic of the red filter 30R with problems, light was slightly transmitted in a wavelength range of 550 to 600 nm. Meanwhile, referring to FIG. 6 showing the characteristic of luminosity in the green display of the LCD 72, the peak of the characteristic of luminosity was in the vicinity of a wavelength of 550 nm and the characteristic of luminosity was even at a wavelength of about 600 nm. It is assumed that the green light was unintentionally transmitted through the red filter 30R with problems though slightly, so that the above result was obtained. Especially for human eyes, green has a high characteristic of luminosity as compared to red (i.e., green is more easily perceived than red), which has an influence on the result.

As for wavelength transmission characteristics of the green filter 30G, there was not observed any notable difference when the green filter 30G was used in the subjective refractive power measurement apparatus 60 or the red and green spectacles. However, green filters 30G also have various characteristics, and green filters 30G of different apparatus manufacturers could result in the same type of problem as the red filter 30R.

In order to solve the above problems, the optotype presenting apparatus according to the preferred embodiment of the present invention has a plurality of color adjustment data in which set values of the luminance levels of the RGB components (luminance and hue) of each of the optotypes constituting the binocular visual performance test chart to be displayed on the LCD 72 are set at a plurality of levels, and one of the color adjustment data is selected. In the following description, switching is made between two stages of a High mode and a Low mode for selecting display colors of the binocular visual performance test chart. The High mode is intended for the red filter 30R having the wavelength transmission characteristic shown in FIG. 5B (i.e., the red filter with no problems) and the Low mode is intended for the red filter 30R having the wavelength transmission characteristic shown in FIG. 5A (i.e., the red filter with problems). A selection signal for selecting either of the High mode and the Low mode is inputted by operation of the switches of the function switch 73.

In the High mode, the luminance levels of the RGB components (the color adjustment data) of each of the optotypes are set as follows. It should be noted that the RGB components of each of the optotypes to be displayed on the LCD 72 are arranged so that their luminance levels can be varied from the level 0 to the level 31 as described above. The level 31 is the highest level. The luminance levels of the RGB components of each of the white background and the white optotype are set so that (R,G,B)=(31,31,31) those of the green optotype are set so that (R,G,B)=(0,31,0), and those of the red optotype are set so that (R,G,B)=(31,0,0). The luminance levels of the RGB components of each of the black background and the black optotype are set so that (R,G,B)=(0,0,0).

In the Low mode, the luminance levels of the RGB components of each of the optotypes (the color adjustment data) differ according to the types of test chart, for example, differ between the Worth four-point test chart shown in FIG. 3A in which the red and green optotypes are provided on the black background and the cross phoria test chart shown in FIG. 4A in which the red and green optotypes are provided on the white background.

In the case of the black background type, the luminance levels of the RGB components of the white optotype are set so that (R,G,B)=(16,16,16), those of the green optotype are set so that (R,G,B)=(0,13,0), and those of the red optotype are set so that (R,G,B)=(25,0,0). As in the case of the High mode, the luminance levels of the RGB components of each of the black background and the black optotype are set so that (R,G,B)=(0,0,0).

Thus, in the case of the black background type, the luminance levels of the RGB components of the green optotype (the optotypes 104 and 105 shown in FIG. 3A) are lowered, so that green light which could be unintentionally transmitted through the red filter 30R of FIG. 5A is decreased, and the green optotype can easily merge with the background. In order to have a luminance balance between the green optotype and the white optotype which is visually perceived in green when observed through the green filter 30G, the luminance levels of the RGB components of the white optotype are also lowered in accordance with the lowering of the luminance levels of the RGB components of the green optotype. In addition, in order to have a luminance balance between the red optotype and the green optotype, the luminance levels of the RGB components of the red optotype are lowered.

In the case of the white background type, the luminance levels of the RGB components of each of the white background and the white optotype are set so that (R,G,B)=(28,28,28), those of the green optotype are set so that (R,G,B)=(0,29,0), and those of the red optotype are set so that (R,G,B)=(31,15,15). As in the case of the High mode, the luminance levels of the RGB components of each of the black background and the black optotype are set so that (R,G,B)=(0,0,0).

Thus, in the case of the white background type, when the red optotype is displayed, not only the R (red) component but also the G (green) and B (blue) components are varied in their luminance levels in order to vary a hue (color tones: combination of the RGB components) of the display. In addition, all of the luminance levels of the RGB components of each of the white background and the white optotype are slightly lowered. Accordingly, when the red optotype is observed through the red filter 30R having the wavelength transmission characteristic shown in FIG. 5A, the red optotype can easily merge with the background which is visually perceived in red. In addition, the balance between the red optotype and the green optotype is obtained by slightly lowering the luminance levels of the RGB components of the green optotype in accordance with the red optotype becoming visually perceived in lighter red.

The set values of the luminance levels of the RGB components (the color adjustment data) of each of the optotypes in the High mode and the Low mode as described above are previously stored in the memory 76.

FIG. 7 is a table showing a list of test charts subjected to switching between the High mode and the Low mode. Examples of the binocular visual performance test chart subjected to switching between the High mode and the Low mode include the test charts as described above, a cross phoria test chart with no fixation target, an aniseikonia test chart, a cross-ring test chart for a phoria test, a cyclophoria test chart, and a stereoscopic vision test chart. In FIG. 7, the test charts subjected to switching between the High mode and the Low mode are assigned a value 1, and the test charts not subjected to switching are assigned a value 0, and the assigned values are stored in the memory 76. In the cross phoria test chart, the aniseikonia test chart and the cyclophoria test chart, switching can be made between the white background type and the black background type on the parameter setting screen displayed on the LCD 72 by operation of the function switch 73. The stereoscopic vision test chart is set to be the white background type.

The test chart with the red and green displays includes a red-green test chart 140 for testing overcorrection at the time of a refractive power test as shown in FIG. 8. The red-green test chart 140 comprises a left-side red background 141R, a black optotype 142a consisting of letters and symbols provided on the left-side red background 141R, a right-side green background 141G, and a black optotype 142b consisting of letters and symbols provided on the right-side green background 141G. In the test using the test chart 140, saturation of the black optotype 142a on the red background 141R and saturation of the black optotype 142b on the green background 141G are compared, and an overcorrection test is performed by checking whether or not both of them are similarly visually perceived. Though the red-green test chart 140 includes the red and green optotypes, the test using the red-green test chart 140 is not subjected to switching between the High mode and the Low mode of the luminance levels (hue) of the RGB components of each of the optotypes because it is performed without using the red filter 30R and the green filter 30G. To be specific, in the case of displaying the red-green test chart 140, predetermined set values of the luminance levels of the RGB components of the display colors are previously stored in the memory 76, are read by the control unit 75, and are displayed on the LCD 72. A polarized red-green test chart is the same type of test chart. Also in the case of the visual acuity test chart, predetermined set values of the luminance levels of the RGB components of the display colors of the LCD 72 are previously stored in the memory 76.

The luminance levels of the RGB components (color adjustment data) of the red-green test chart 140 are set as follows. The luminance levels of the RGB components of the red background 141R are set so that (R,G,B)=(31,0,0) those of the green background 141G are set so that (R,G,B)=(0,31,0), and those of each of the black optotypes 142a and 142b are set so that (R,G,B)=(0,0,0). The visual acuity test chart comprises a Landolt ring black optotype on a white background (see FIG. 1). The luminance levels of the RGB components of the white background are set so that (R,G,B)=(31,31,31), and those of the black optotype are set so that (R,G,B)=(0,0,0).

Next, a description of a procedure for switching the binocular visual performance test chart to be displayed on the LCD 72 to the Low mode. When any one of the switches 73a to 73d of the function switch 73 is pressed, a parameter setting screen 80 is displayed on the LCD 72 as shown in FIG. 9. The parameter setting screen 80 shows items 82 for setting various parameters of the apparatus. An operating key group 84 is displayed in the lower portion of the parameter setting screen 80. An UP key 84a corresponds to the switch 73a, a DOWN key 84b corresponds to the switch 73b, a CHANGE SCREEN key 84c corresponds to the switch 73c, and a CHANGE key 84d corresponds to the switch 73d.

By operation of the UP key 84a and the DOWN key 84b, a cursor 81a is moved to the item "Brightness R/G", and the CHANGE key 84d is pressed to change the indication to "LOW". Then, by operation of the DOWN key 84b, the cursor 81a is moved to an "EXIT" key 83, and the CHANGE key 84d is pressed to exit the setting screen, which completes changing the settings to the Low mode. Accordingly, a plurality of binocular visual performance test charts are switched altogether to the Low mode.

If the red filter 30R and/or the green filter 30G do not require being switched to the Low mode, they are used in the High mode. In the High mode, for example in the test chart 100 shown in FIG. 3A, the optotypes 102 and 103 are visually perceived in bright red when observed through the red filter 30R, and the optotypes 104 and 105 and the optotype 103 are visually perceived in bright green when observed through the green filter 30G, so that the difference between them becomes clear. Thus, accuracy of the test is improved.

In an actual test, when the test chart is selected by the switch 4a of the remote controller 4, the selection signal is inputted to the control unit 75 via the transmitting portion 4c and the receiving unit 74. The control unit 75 reads the configuration data and the color adjustment data of the selected test chart from the memory 76 based on the selection signal of the test chart. If the binocular visual performance test chart is selected as the test chart, the control unit 75 reads, additionally based on the selection signal of the High mode or the Low mode, the color adjustment data corresponding to the selected mode from the memory 76. Then, the control unit 75 controls the LCD 72 to display the test chart based on the read configuration data and color adjustment data of the test chart. If the test chart selected by the switch 4a is not the binocular visual performance test chart but the visual acuity test chart, the red-green test chart 140 or other test chart, the selection between the High mode and the Low mode is irrelevant. In such a case, the control unit 75 reads predetermined color adjustment data corresponding to the selected test chart from the memory 76, and controls the LCD 72 to display the selected test chart.

Variations can be made to the above-described preferred embodiment of the invention. For example, though the luminance levels of the RGB components of each of the optotypes in the Low mode are previously set by the apparatus manufacturer, an examiner may change the luminance levels in accordance with characteristics of a red filter and/or a green filter of another apparatus manufacturer. In such a case, the parameter setting screen 80 is displayed on the LCD 72, the item "Brightness R/G" is selected, and the Low mode is selected by using the CHANGE key 84d. Because the set values previously set by the apparatus manufacturer are stored as the Low mode, the examiner changes and corrects the previously stored set values.

Figure 10A:
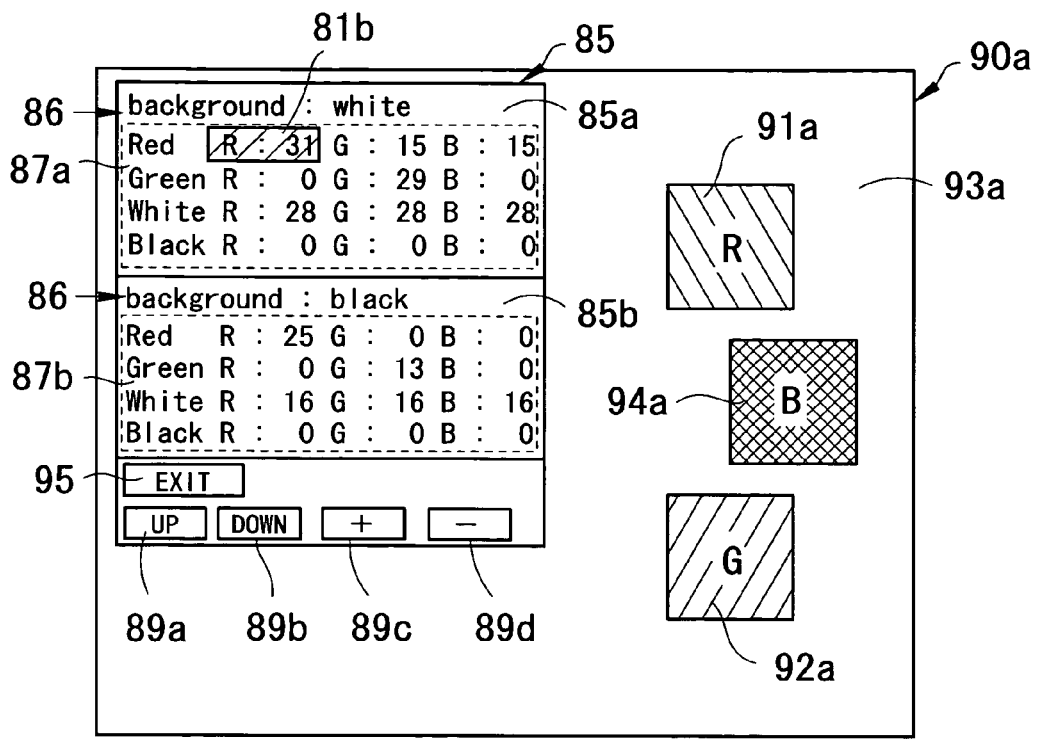
FIG. 10A shows an example of a screen used when set values for color adjustment are varied in a test chart with a white background.
Figure 10B:
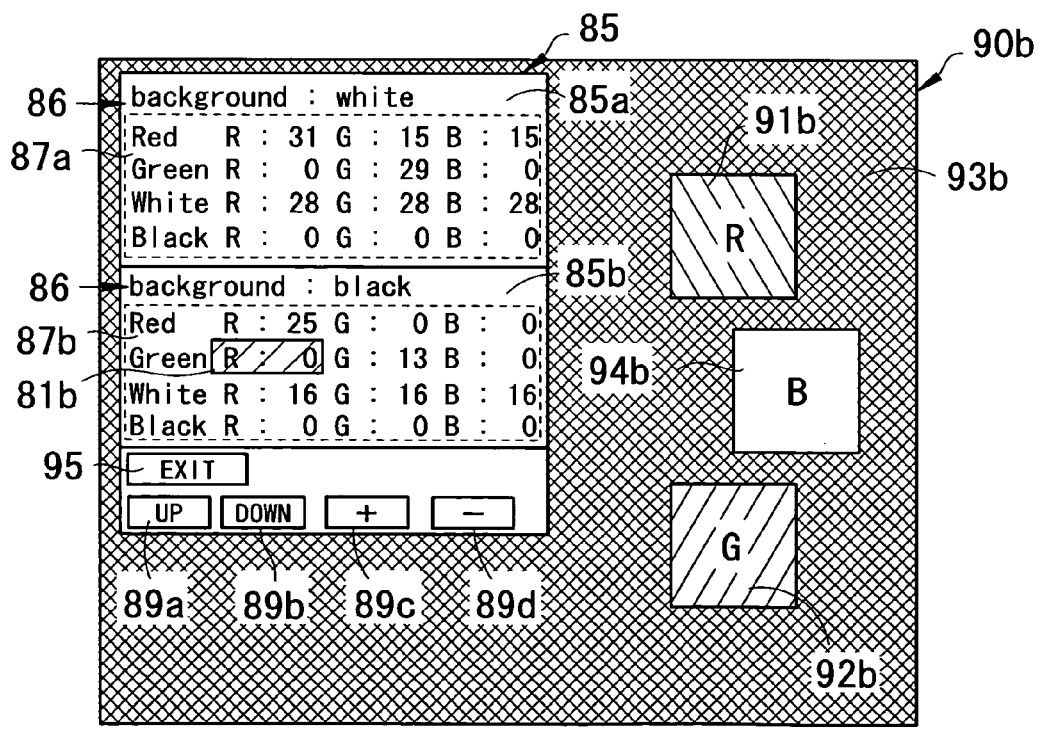
FIG. 10B shows an example of a screen used when set values for color adjustment are varied in a test chart with a black background.

When the switch 73c is pressed for a while with the Low mode selected, a confirmation screen 90a for a white background (hereinafter, referred to as a confirmation screen (white) 90a) shown in FIG. 10A or a confirmation screen 90b for a black background (hereinafter, referred to as a confirmation screen (black) 90b) shown in FIG. 10B is displayed. A Low mode setting screen 85 is displayed on each of the confirmation screen (white) 90a and the confirmation screen (black) 90b. Which of the confirmation screen (white) 90a and the confirmation screen (black) 90b is to be displayed is determined according to the position of a cursor 81b on the Low mode setting screen 85.

The Low mode setting screen 85 comprises a condition setting screen 85a for a white background (hereinafter, referred to as a setting screen (white) 85a) and a condition setting screen 85b for a black background (hereinafter, referred to as a setting screen (black) 85b). A text display 86 indicating the background color is provided in the upper potion of each of the setting screen (white) 85a and the setting screen (black) 85b. Condition setting items 87a and 87b for selecting colors of the optotypes are provided on the setting screen (white) 85a and the setting screen (black) 85b, and the luminance levels of the RGB components of each of the optotypes can be set by using the items. When setting the luminance levels, any one of the RGB components next to the items 87a and 87b is selected by moving the cursor 81b by operation of the switch 73a corresponding to an UP key 89a for moving the cursor 81b to the next position and the switch 73b corresponding to a DOWN key 89b for moving the cursor 81b to the previous position. Then, the luminance levels are adjusted to be desired values by operation of the switch 73c corresponding to a plus key 89c and the switch 73d corresponding to a minus key 89d.

When the confirmation screen (white) 90a shown in FIG. 10A is displayed, the examiner checks visibility of a red screen 91a, a green screen 92a, a white screen 93a, and a black screen 94a through the red filter 30R and/or the green filter 30G. In addition, when the confirmation screen (black) 90b shown in FIG. 10B is displayed, the examiner checks visibility of a red screen 91b, a green screen 92b, a black screen 93b, and a white screen 94b through the red filter 30R and/or the green filter 30G. If the red screen and/or the green screen do not disappear well, the luminance levels are inputted again as described above, and visibility is checked again through the red filter 30R and/or the green filter 30G. Upon completion of inputting the luminance levels, the switch 73c is pressed for a while and the settings are stored. Then, the cursor 81b is moved to an "EXIT" key 95, and the switch 73d is pressed in order to exit the setting screen.

As mentioned above, the examiner can perform color adjustment of such as luminance and hue while checking visibility of the red optotype and/or the green optotype through the red filter 30R and/or the green filter 30G. Therefore, the binocular visual performance test chart can be changed so as to have proper visibility in accordance with different characteristics of the red filter 30R and/or the green filter 30G.

In addition, in changing the color adjustment data of such as luminance and hue of the binocular visual performance test chart, not only the two stages of the High mode and the Low mode but also three stages of High/Middle/Low modes or five stages from 5 to 1 in accordance with the degree of luminance may be used so that a plurality of luminance conditions may be stored for each of the items.

Though changing the set values of the color adjustment data of such as luminance and hue of the binocular visual performance test chart is performed altogether on a plurality of test charts in the above description, set values which are changed for each test chart by the examiner may be stored.

In addition, though the luminance levels of the RGB components of the binocular visual performance test chart are varied in accordance with different characteristics of the red filter and/or the green filter in the above description, the color adjustment data such as the luminance levels of the RGB components of the test chart may be varied according to the environment where the optotype presenting apparatus is placed. For example, brightness of red and brightness of green are visually perceived differently in a bright room and a dark room; therefore, the color adjustment data of such as luminance and hue of the binocular visual performance test chart is accordingly changed. It is convenient to provide a brightness detecting sensor and arrange the control unit 75 to change the display colors of the LCD 72 based on the detected brightness.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. An optotype presenting apparatus comprising:
   a color display comprising a number of arranged pixels comprising red, green, and blue filters;
   a first memory which stores data on a plurality of test charts including a visual acuity test chart and a red-green binocular visual performance test chart, wherein the binocular visual performance test chart includes a black background or a white background, a red optotype, and a green optotype and is used in a binocular visual performance test performed with a red filter placed in front of one of eyes of an examinee and a green filter placed in front of the other eye;
   a test chart selecting unit which selects from the test charts stored in the first memory a test chart to be displayed on the display;
   a color adjusting unit which varies and adjusts respective luminance levels of red, green, and blue components of at least one of the red optotype and the green optotype;
   a second memory which stores a plurality of pieces of luminance information which is adjusted with respect to at least one of the red optotype and the green optotype;
   a color selecting unit which selects one of the plurality of pieces of luminance information stored in the second memory when the binocular visual performance test chart is selected; and
   a display control unit which controls the display to display the selected test chart and controls, when the binocular visual performance test chart is selected, the display to display the red optotype and the green optotype comprising an optotype adjusted based on the selected piece of luminance information together with the black background or the white background.

2. The optotype presenting apparatus according to claim 1, wherein the color adjusting unit comprises a color adjusting screen on which visibility of at least one of the red optotype and the green optotype on the black background or the white background can be checked during the adjustment.

3. The optotype presenting apparatus according to claim 1, wherein the first memory stores, as data on the binocular visual performance test chart, data on a plurality of red optotypes having different luminance levels of red, green, and blue components.

4. The optotype presenting apparatus according to claim 1, wherein the first memory stores, as data on the binocular visual performance test chart, data on a plurality of green optotypes having different luminance levels of red, green, and blue components.

5. An optotype presenting apparatus comprising:
   a color display comprising a number of arranged pixels;
   a first memory which stores data on a plurality of test charts including a visual acuity test chart and red-green binocular visual performance test charts, wherein the binocular visual performance test charts are used in a binocular visual performance test performed with a red filter placed in front of one of eyes of an examinee and a green filter placed in front of the other eye;
   a test chart selecting unit which selects from the test charts stored in the first memory a test chart to be displayed on the display;
   a second memory which stores first color adjustment information on the binocular visual performance test charts having a color adjusted in accordance with a first red filter having a predetermined wavelength characteristic and a first green filter having a predetermined wavelength characteristic, and second color adjustment information on the binocular visual performance test charts having a color adjusted in accordance with at least one of a second red filter having a wavelength characteristic different from that of the first red filter and a second green filter having a wavelength characteristic different from that of the first green filter;
   a color selecting unit which selects one of the first color adjustment information and the second color adjustment information; and
   a display control unit which controls, when one of the binocular visual performance test charts is selected by the test chart selecting unit, the display to display the selected binocular visual performance test chart based on the data stored in the first memory and the color adjustment information selected by the color selecting unit.

6. The optotype presenting apparatus according to claim 5 further comprising input means which displays a setting screen for setting the second color adjustment information on the screen, and inputs desired luminances of red, green, and blue components.

7. The optotype presenting apparatus according to claim 6, wherein the input means inputs luminances for each of a case where the binocular visual performance test chart has a white background and a case where the binocular visual performance test chart has a black background.

8. The optotype presenting apparatus according to claim 6, wherein the input means inputs luminances common to a plurality of the binocular visual performance test charts.

9. The optotype presenting apparatus according to claim 6, wherein the input means inputs luminances for each of a plurality of the binocular visual performance test charts.

10. The optotype presenting apparatus according to claim 5, wherein the second memory stores a plurality of pieces of the first color adjustment information.

11. The optotype presenting apparatus according to claim 5, wherein the second memory stores a plurality of pieces of the second color adjustment information.

* * * * *